United States Patent
Örning

(10) Patent No.: US 7,294,514 B2
(45) Date of Patent: Nov. 13, 2007

(54) DIAGNOSTIC METHOD FOR ALZHEIMER'S DISEASE BASED ON HOLO-TRANSCOBALAMIN II

(75) Inventor: Lars Örning, Oslo (NO)

(73) Assignee: Axis Shield ASA, Oslo (NO)

( * ) Notice: Subject to any disclaimer, the term of this patent is extended or adjusted under 35 U.S.C. 154(b) by 0 days.

(21) Appl. No.: 10/332,041

(22) PCT Filed: May 22, 2001

(86) PCT No.: PCT/GB01/02306

§ 371 (c)(1),
(2), (4) Date: Jun. 9, 2003

(87) PCT Pub. No.: WO02/03074

PCT Pub. Date: Jan. 10, 2002

(65) Prior Publication Data

US 2004/0014230 A1    Jan. 22, 2004

(30) Foreign Application Priority Data

Jul. 4, 2000    (GB)    ................... 0016460.8

(51) Int. Cl.
*G01N 33/48*    (2006.01)

(52) U.S. Cl. .................. 436/63; 436/86; 536/26.4; 514/52

(58) Field of Classification Search .................. 436/63, 436/84, 73, 74, 86; 536/26.4; 514/52; 422/61; 435/975, 810

See application file for complete search history.

(56) References Cited

U.S. PATENT DOCUMENTS

| 4,273,757 A | * | 6/1981 | Selhub et al. ................ 436/505 |
| 4,680,273 A | | 7/1987 | Herbert |
| 6,417,006 B1 | * | 7/2002 | Sundrehagen ................ 436/84 |

FOREIGN PATENT DOCUMENTS

WO    WO 00/17659 A1    3/2000

OTHER PUBLICATIONS

Johnston et al. Journal of the American Geriatrics Society, vol. 45 (6), Jun. 1997, pp. 779-780.*
Clarke Robert et al: "Folate, vitamin B12, and serum total homocysteine levels in confirmed Alzheimer disease." Archives of Neurology, vol. 55, No. 11, Nov. 1998, pp. 1449-1455.
Kristensen Marianne O et al: "Serum cobalamin and methymalonic acid in Alzheimer dementia." ACTA Neurologica Acandinavica, vol. 87, No. 6, 1993, pp. 475-481.
Basun Hans et al: "Cobalamin levels are not reduced in Alzheimer's disease: Results from a population-based study." Journal of the American Geriatrics Society, vol. 42, No. 2, 1994, pp. 132-136.

* cited by examiner

*Primary Examiner*—Maureen M. Wallenhorst
(74) *Attorney, Agent, or Firm*—Bacon & Thomas PLLC

(57) ABSTRACT

The invention provides a diagnostic or prognostic assay method for Alzheimer's Disease by assaying a body fluid sample or a test sample derived therefrom for holo-trancobalamin II.

14 Claims, No Drawings

DIAGNOSTIC METHOD FOR ALZHEIMER'S DISEASE BASED ON HOLO-TRANSCOBALAMIN II

The present invention relates to an assay method for diagnosis or prognosis of Alzheimer's Disease, more particularly an assay involving the determination of holo-transcobalamin II (holoTCII) in a body fluid, and to assay kits for use in such assay methods.

Alzheimer's disease (AD) is the most common cause for cognitive loss in older adults, the second most common being mixed dementia, a combination of AD pathology and cerebral infarcts. AD is a neurodegenerative disorder characterized by neuropathological features including neuronal loss, the formation of neurofibrillary tangles, and amyloid deposits (senile plaques). AD is a complex disorder and the cascade of gradual changes, which often take more than a decade to fully develop, makes it difficult to diagnose. Certain diagnosis can only be made at autopsy when brain tissue can be examined under microscope. Usually, diagnosis of AD in the living patient is based on medical history, physical examination, and cognitive tests.

AD usually affects people older than the age of 65, but can affect also those younger than 40 years. At age 65 the prevalence is about 2% which rises steadily with age to about 20% at the age of 80.

Although only age and heredity are proven risk factors for AD, several epidemiological studies have suggested vascular factors, including hypertension and diabetes may influence the risk of developing AD (see Hachinski and Munoz, Ann. N.Y. Acad Sci 826: 1-6, (1997)). It has been suggested that the microvascular abnormalities found in AD could be brought about by chronic exposure to elevated levels of plasma homocysteine, in its turn caused by moderate deficiencies in folate and cobalamin or Vitamin B12 (VB12) (see Regland et al Dementia, 1: 272-277 (1990) and McCaddon et al., Int J Geriatr Psychiatry, 13: 235-239 (1998)).

VB12 is a water soluble vitamin which forms part of the vitamin B complex found in foods and is an essential vitamin necessary for cell proliferation and metabolism. The core molecule consists of a corrin ring of four pyrole units which surround the central cobalt atom. VB12 is the only vitamin which cannot be synthesised by animals or plants and must be absorbed from food in the gut. It can however be stored in the liver. It is synthesised by micro-organisms, in particular by anaerobic bacteria and yeasts.

VB12 functions in vivo as a co-enzyme and VB12 enzymes catalyse three types of reaction; (i) intra-molecular rearrangements, for example, the formation of succinyl CoA from L-methylmalonyl CoA, (ii) methylations, for example, the formation of methionine by methylation of homocysteine and (iii) reduction of ribonucleotides to deoxyribonucleotides in some micro-organisms. In mammals, only two enzymic reactions, those specifically mentioned in (i) and (ii) above are known to require VB12 as a co-enzyme.

In the process of digestion, a salivary protein called haptocorrin, hereinafter referred to as HC (which is also referred to in the art as R-binder or transcobalamins I and III collectively) binds VB12 in the upper gastrointestinal tract forming a complex which passes through the stomach. Pancreatic enzymes digest the VB12-haptocorrin (holo-HC) complex in the ileum, liberating VB12 which is then bound to a protein called intrinsic factor, which is secreted by the gastric mucosa, to form a further complex. The VB12-intrinsic factor complex binds to a specific receptor in the lining of the terminal ileum, whereupon it is dissociated by a releasing factor and the VB12 transported actively across the membrane of the ileum into the blood stream.

VB12 does not circulate in the body in a free form in an appreciable amount. Probably 99% or so of VB12 is bound by one of the transcobalamin proteins (TCI, II and III) or albumin.

The protein believed to be responsible for transporting VB12 to target tissues is transcobalamin II (TC II), a critical trace protein without which V12 cannot cross cell membranes. Despite this important metabolic function only about 6-25% of VB12 in the serum is bound to TC II and most is carried by HC. TC II is a single chain polypeptide of 45 kDa found primarily in serum, seminal fluid and cerebro-spinal fluid. VB12 bound TC II (i.e. holo-TC II), attaches to specific receptors on cell membranes and once bound, the holo-TC II complex is taken into cells by pinocytosis.

TC II is synthesised by the liver, vascular endothelium, enterocytes, macrophages and fibroblasts and circulates predominantly as apo-TC II, i.e. lacking bound VB12. It has a short half life of approximately 90 minutes.

Since VB12 must be absorbed from food, any conditions which result in impaired gastric function, for example, gastroenteritis or conditions resulting in gastric atrophy, or an inability to produce functional haptocorrin, intrinsic factor, releasing factor, TC II or TC II receptors, can result in impaired uptake of VB12 and resultant deficiency.

Certain population sub-groups, for example the aged, pregnant women, patients with chronic or acute gastrointestinal disease, those suffering from certain autoimmune diseases, those with a family history of pernicious anaemia and AIDS sufferers, are particularly prone to VB12 deficiency.

The clinical manifestations of VB12 deficiency are varied and numerous but primarily involve, anaemia, megaloblastic haematopoiesis and functional and structural disorders of the nervous system.

At the molecular level, VB12 deficiency leads to decreased levels of tetra-hydrofolate and S-adenosyl methionine and increased levels of methyl-malonic acid, methyl-tetra-hydrofolate, and homocysteine. At the physiological level, it leads to potentially irreversible nerve damage and/or severe anaemia. The neuropathy arising from VB12 deficiency gives clinical symptoms similar to those observed for patients with senile dementia of Alzheimer-type. Therefore it is common to measure the total serum VB12 level in patients with dementing illnesses.

Some studies have found lower concentrations of total serum VB12 in patients with AD (see Cole and Prchal, Age Ageing 13: 101-105 (1984) and Clarke et al., Arch. Neurol 55: 1449-1455 (1998)), others have seen no significant difference (see Crystal et al., J. Am. Geriatr Soc. 42: 933-936 (1994), Basun et al., J. Am Geriatr Soc. 42: 132-136 (1994) and Joosten et al., J. Gerontol 52: M76-M79 (1997)). Much controversy exists on the subject of the association of AD with VB12 deficiency.

While holoTCII deficiency has been acknowledged as indicative of VB12 deficiency (e.g. in the elderly and even for AD sufferers) and hence as an indicator that nutritional therapy to counteract the VB12 deficiency is desirable, there has been no suggestion that holoTCII deficiency is an indicator for AD as such.

We have now found that there is a significantly lower holoTCII count for patients with confirmed AD as compared to healthy volunteers of the same age, i.e. a matched control group, and that the correlation between AD and reduced holoTCII is more significant than any correlations between AD and reduced total serum VB12 or total homocysteine.

Viewed from one aspect therefore the present invention provides a diagnostic or prognostic assay method for Alzheimer's Disease which method comprises assaying a body fluid sample or a test sample derived therefrom for holo transcobalamin II, comparing the holo-trancobalamin II level determined with a pre-determined threshold value and assigning the assay result as indicative or non-indicative of Alzheimer's disease.

Methods of assaying for holo TCII are known and are described for example in WO 00/17659, U.S. Pat. No. 4,680,273, Herbert et al. Am. J. Hematol. 34: 132-139 (1990), Wickramasinghe et al. J. Clin. Pathol. 46: 537-539 (1993), Carmel Am. J. Clin. Pathol. 62: 367-372 (1974), Herzlich et al. Lab. Invest. 58: 332-337 (1988), Vu et al. Am. J. Hematol. 42: 202-211 (1993), Lindemans et al. Clin. Chim. Acta 132: 53-61 (1983), Kapel et al. Clin. Chim. Acta 172: 297-310 (1988), Benhayoun et al. Acta Haematol. 89: 195-199 (1993), Toft et al. Scan. J. Clin. Lab. Invest. 54: 62 (1994) and Kuemmerle et al. Clin. Chim. 38: 2073-2077 (1992), the contents of which are hereby incorporated by reference. These techniques, preferably that of Kuemmerle et al. (supra) and more preferably that of WO 00/17659, may be used in the assay method of the present invention.

The body fluid sample used in the method of the invention may be any human body fluid that normally contains holoTCII, e.g. seminal fluid or cerebrospinal fluid; however it is preferably a blood sample. More preferably the sample assayed in the method of the invention is a blood derived sample, e.g. a plasma or more particularly a serum sample. Such samples may be taken from patients suspected of having AD or confirmed as having AD or may be taken from patients, generally elderly patients, as part of a routine screening or health check.

Assaying for holoTCII using the method of the invention may involve generation of a qualitative, semi-quantitative or quantitative indication of holoTCII in the sample tested or in the body fluid it is derived from, e.g. in blood, plasma or most especially serum. The sample may be treated prior to being used in the assay method of the invention, for example it may be diluted by adding a buffer or other aqueous medium and may be stored or preserved for example by chilling or freezing prior to analysis.

Determination of an absolute value of concentration (e.g. in pM concentration) of holoTCII is desirable but may not be necessary as it may be sufficient simply to indicate whether the holoTCII, concentration is above or below one or more predetermined threshold values indicative of presence or severity of AD. The method will however generally require calibration against holoTCII values determined for control groups, in particular control groups of healthy people of the same age range and preferably also confirmed AD sufferers of the same age range. The method may thus also involve the step of comparing the assayed holoTCII value with such predetermined calibration values so as to categorise or stage the human source of the sample as probably having or not having AD or as having AD at a particular stage of development. Typically a holoTCII serum concentration in elderly patients (e.g. aged over 60, more particularly 70) of below 70 pM, more particularly below 60 pM may be indicative of AD.

In the method of the invention, the sample is preferably also assayed for total VB12, optionally also for total homocysteine and optionally also for folate.

Viewed from a further aspect the invention also provides an assay kit for use in the performance of a method according to the invention, said kit comprising an immobilized or immobilizable specific binding ligand for TCII or holo-TCII;

preferably a holo-TCII solution of known concentration and more preferably a set of such solutions having a range of holo-TCII concentrations;

optionally, a release agent to release VB12 from holo-TCII;

optionally a labelled ligand; and a calibrator for threshold holoTCII concentration indicative of AD or AD severity as a function of age.

Typically, calibration samples having holo-TCII contents of 0 to 200 pmol/l will be used. The reference range within which the value for holoTCII will generally be found is 30 to 160 pmol/l.

Such assay kits, omitting only the calibrator, are described in WO 00/17659.

The invention will now be described further with reference to the following non-limiting Example.

EXAMPLE

HoloTCII, total serum vitamin B12 (tVB12), and total homocysteine (Hcy) levels were measured in serum samples taken from (i) 20 persons with confirmed Alzheimer-type dementia and (ii) 20 healthy volunteers of the same age group (matched controls).

HoloTCII concentrations were determined by HoloTC-RIA, a system for measuring holoTCII available from Axis-Shield ASA, Oslo, Norway and described in WO 00/17659.

Results were analyzed both with respect to mean values and odds-ratios. Odds ratios were calculated as follows: cases with "out of normal" values/total cases of the Alzheimer group divided with the same ratio for the control group. A value greater than one (1) indicates that a risk may exist. For holoTCII, 35 pM was used as cut-off and for tVB12, 150 pM. Values above 35 and 150 pM, respectively, were considered as being within the normal range. For tHCy, values below 15 µM were deemed within normal range.

The results are set out in the table below.

| Parameter | Group | Total | Mean | Significance* | Cases | Odds ratio |
|---|---|---|---|---|---|---|
| HoloTC | control | 20 | 83 pM | | 1 | — |
| | AD¶ | 20 | 52 pM | P < 0.005 | 5 | 5.0 |
| tVB12 | control | 20 | 263 pM | | 2 | — |
| | AD | 20 | 296 pM | P < 0.4 | 1 | 0.5 |
| tHCy | control | 13 | 13.4 µM | | 4 | — |
| | AD | 17 | 15.2 µM | P < 0.3 | 8 | 1.5 |

*Man~Whitney;
¶AD, Alzheimer's disease

Serum holoTCII levels were significantly lower in patients with confirmed Alzheimer type dementia; the mean value was significantly lower and the odds ratio was 5 fold increased in the disease group.

Serum tHCy levels were higher in the patient group, albeit not significantly, and also had an odds ratio of 1.5. The reason for tHCy not obtaining significance is most likely is due to factors other than holoTCII that also influence tHCy concentrations, such as folate and vitamin B6 levels and kidney status.

tVB12 was somewhat higher in the disease group, albeit not significantly, a finding also seen in the odds ratio, which was less than 1.0.

The invention claimed is:

1. A diagnostic or prognostic assay method for assessing the risk of Alzheimer's Disease in a patient which method comprises taking a body fluid sample from a patient, assaying the body fluid sample or a test sample derived therefrom for holo-transcobalamin II to provide a holo-transcobalamin II concentration, and relating the holo-transcobalamin II concentration to one or more predetermined threshold values indicative of the presence or severity of Alzheimer's Disease wherein lower holo-transcobalamin II concentration relative to the threshold values is indicative of a higher risk of the presence or greater severity of Alzheimer's Disease.

2. A method as claimed in claim 1 wherein said body fluid sample is a blood sample.

3. A method as claimed in claim 2 wherein said blood sample is also assayed for at least one of total vitamin $B_{12}$, total homocysteine, or folate.

4. A method as claimed in claim 1 where said test sample is a serum sample.

5. A method as claimed in claim 4, wherein said serum sample is also assayed for at least one of total vitamin $B_{12}$, total homocysteine, or folate.

6. A method as claimed in claim 1 wherein said body fluid or test sample is also assayed for total vitamin $B_{12}$.

7. A method as claimed in claim 6 wherein said body fluid or test sample is also assayed for total homocysteine.

8. A method as claimed in claim 6 wherein said body fluid or test sample is also assayed for folate.

9. A method as claimed in claim 1 wherein said body fluid or test sample is also assayed for total homocysteine.

10. A method as claimed in claim 9 wherein said body fluid or test sample is also assayed for folate.

11. A method as claimed in claim 1 wherein said body fluid or test sample is also assayed for folate.

12. A method as claimed in claim 1 wherein the assay of said body fluid sample or test sample comprises analysis of serum concentration, and wherein a serum concentration of holo-transcobalamin II of below 70 pM is classed as indicative of a risk of Alzheimer's Disease.

13. A method as claimed in claim 1 wherein the assay of said body fluid sample or test sample comprises analysis of serum concentration, and wherein a serum concentration of holo-transcobalamin II of below 60 pM is classed as indicative of a risk of Alzheimer's Disease.

14. A method as claimed in claim 1 wherein the assay of said body fluid sample or test sample comprises analysis of serum concentration, and wherein a serum concentration of holo-transcobalamin II of 35 pM is a cutoff as indicative of a risk of Alzheimer's Disease.

* * * * *